(12) United States Patent
Ben-Hur

(10) Patent No.: US 6,348,453 B1
(45) Date of Patent: Feb. 19, 2002

(54) METHODS FOR TREATING VIRAL INFECTIONS

(75) Inventor: Ehud Ben-Hur, New York, NY (US)

(73) Assignee: New York Blood Center, Inc., Bronx, NY (US)

( * ) Notice: Subject to any disclaimer, the term of this patent is extended or adjusted under 35 U.S.C. 154(b) by 0 days.

(21) Appl. No.: 09/543,607

(22) Filed: Apr. 5, 2000

Related U.S. Application Data

(63) Continuation of application No. 08/841,042, filed on Apr. 29, 1997, now Pat. No. 6,103,706.

(51) Int. Cl.⁷ .............................................. A61K 31/555
(52) U.S. Cl. ........................ 514/185; 424/450; 540/122; 540/131; 540/140
(58) Field of Search .......................... 514/185; 540/122, 540/131, 140; 424/450

(56) References Cited

U.S. PATENT DOCUMENTS

| | | | | |
|---|---|---|---|---|
| 5,120,649 A | * | 6/1992 | Horowitz et al. | ........... 435/173 |
| 5,232,844 A | * | 8/1993 | Horowitz et al. | ........ 435/173.1 |
| 5,277,913 A | * | 1/1994 | Thompson et al. | ......... 424/450 |
| 5,516,629 A | * | 5/1996 | Park et al. | ...................... 435/2 |
| 6,010,890 A | * | 1/2000 | Ben-Hur et al. | ......... 435/173.3 |

* cited by examiner

Primary Examiner—Joseph K. McKane
Assistant Examiner—Joseph Murray
(74) Attorney, Agent, or Firm—Amster, Rothstein & Ebenstein

(57) ABSTRACT

The present invention provides a method for treating a viral infection in a subject in need of such treatment comprising administering to the subject a photosensitizer formulated in a liposome carrier, and exposing the subject to light at a wavelength 20–40 nm greater than the maximum absorption of the photosensitizer at a sufficient dose and duration to treat the viral infection in the subject. The present invention also provides a method for treating a viral infection in a subject in need of such treatment comprising administering to the subject (i) a photosensitizer formulated in a liposome carrier and (ii) at least one quencher, and exposing the subject to light at a sufficient wavelength, dose and duration to treat the viral infection in the subject.

33 Claims, 3 Drawing Sheets

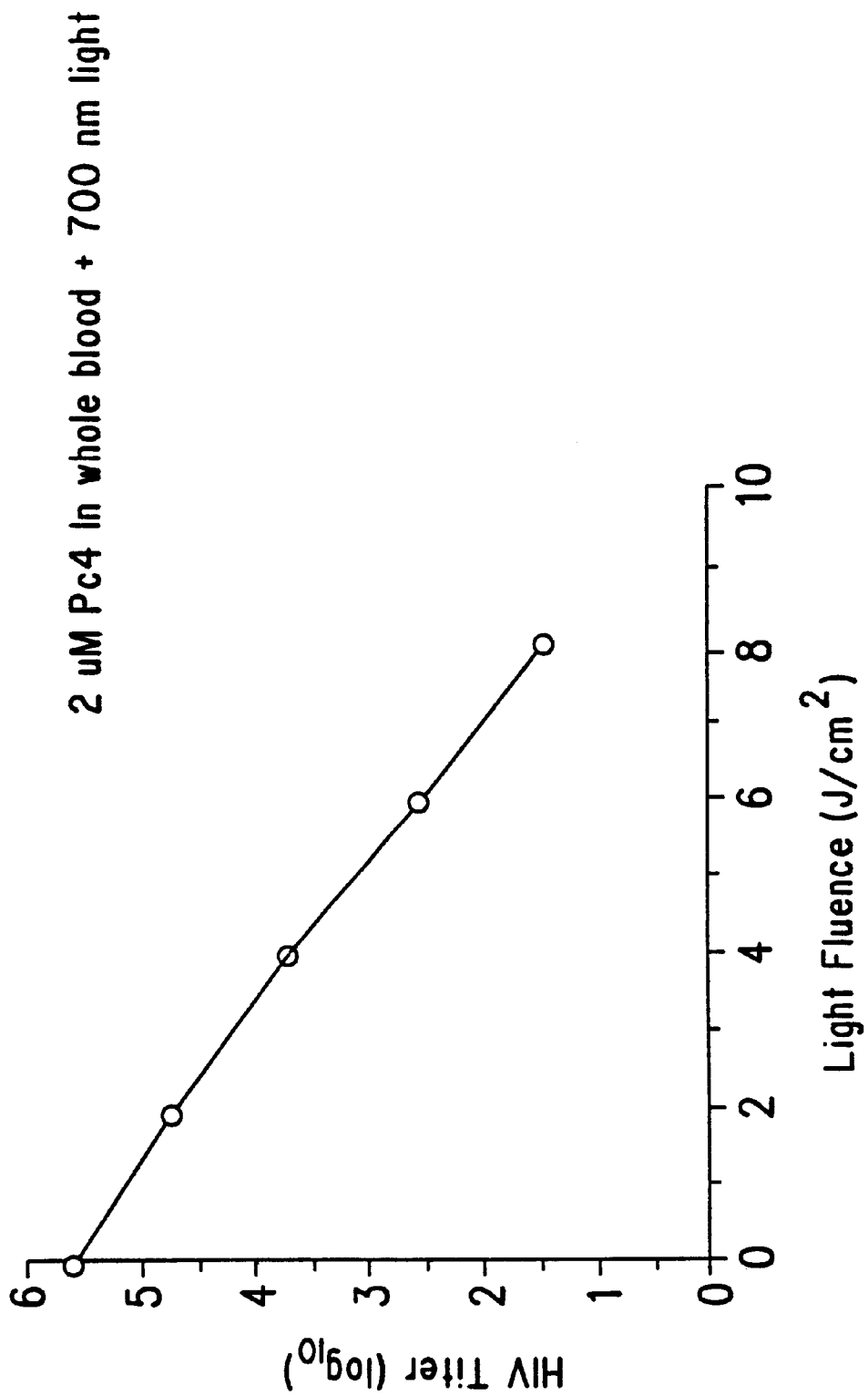

METHODS FOR TREATING VIRAL INFECTIONS

This is a continuation of application Ser. No. 08/841,042, filed Apr. 29, 1997, now U.S. Pat. No. 6,103,706 the contents of which is hereby incorporated by reference.

BACKGROUND OF THE INVENTION

Current treatments for AIDS use drugs; such as azidothymidine (AZT), and other protease inhibitors which inhibit HIV replication. These treatments have only limited efficacy because HIV mutates rapidly and new strains that are drug-resistant eventually develop.

The use of photochemical inactivation procedures are currently used to render blood safe for transfusion. For example, the addition of phthalocyanines such as Pc4 to blood followed by exposure to red light has been shown to effectively reduce viral load in vitro (Margolis-Nunno, H., et al. *Transfusion* 36:743–750 (1996)). Pc4 kills HIV by binding to the viral envelope and producing reacting oxygen species (ROS) upon light activation, which subsequently cause damage to the viral proteins, rendering the virus non-infectious. Because binding of Pc4 to viral membrane is nonspecific, drug-resistant strains cannot arise from this treatment.

Accordingly, if such treatment could be performed on AIDS patients to reduce HIV viremia in their blood, such treatment is expected to be beneficial since a reduced quantity of HIV in plasma is a predictor for enhanced survival of AIDS patients (Mellors, J. W., et al. *Science* 272:1167–1170 (1996)). However, because photo-inactivation is not specific, Pc4 and other photosensitizers, can also bind to red blood cell (RBC) membranes and cause RBC damage. Accordingly, there exists a need for rendering RBC safe while at the same time maintaining good viral kill in vivo.

SUMMARY OF THE INVENTION

The present invention is directed to a method for treating a viral infection, such as HIV, in a subject in need of such treatment, which utilizes photochemical inactivation procedures to reduce the level of infectious virus contained in the blood while simultaneously minimizing the damage done to red blood cells. In this connection, the inventor has found that by incorporating the photosensitizer in a liposome formulation and applying light at a certain wavelength above the maximum absorption of the photosensitizer, a good virus kill can be achieved while minimizing the damage to red blood cells.

In addition, the inventor believes that by incorporating the photosensitizer in a liposome formulation and also administering a quencher alone or in a liposome formulation, the damage to red blood cells also can be minimized.

BRIEF DESCRIPTION OF THE FIGURES

FIG. 3 depicts HIV inactivation in whole blood (spiked with >5.6 $\log_{10}$ HIV; ○) following treatment with liposomal 2 µM Pc4 and 700 nm light at various light fluences (J/cm²) at a fluence rate of 20 mW/cm² at room temperature.

DETAILED DESCRIPTION OF THE INVENTION

Figure 1:
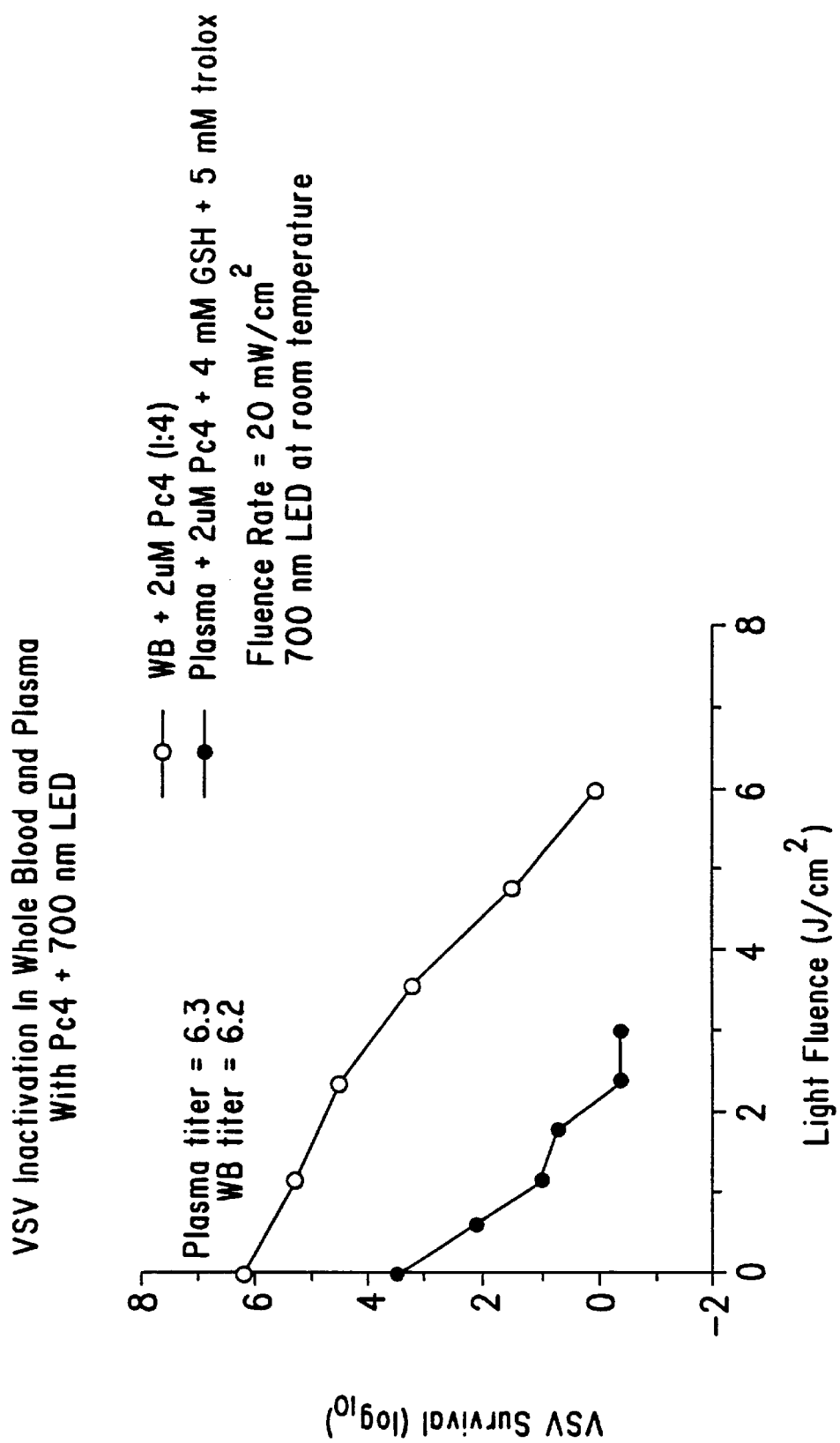
FIG. 1 depicts VSV inactivation in whole blood (spiked with 6.1 $\log_{10}$ VSV; ○) and plasma (spiked with 6.3 $\log_{10}$ VSV; ●) following treatment with liposomal 2 µM Pc4 and liposomal 2 µM Pc4+4 mM GSH+5 mM trolox, respectively, and 700 nm light at various light fluences (J/cm²) at a fluence rate of 20 mW/cm² at room temperature.

The present invention provides a method for treating a viral infection in a subject in need of such treatment. The method comprises administering to the subject a photosensitizer formulated in a liposome carrier, and exposing the subject to light at a wavelength 20–40 nm greater than the maximum absorption of the photosensitizer at a sufficient dose and duration to treat the viral infection in the subject.

The method of the present invention may be used to treat various viral infections caused by viruses including but not limited to human immunodeficiency virus, Cytomegalovirus, Ebstein-Barr virus, Hepatitis B virus, Hepatitis C virus, Herpes Simplex type I and II viruses, and other viruses that circulate in freely in blood, as well as cell-associated viruses. As used herein, "treating" means that the level of infectious virus is reduced in such a manner that the majority of all of the infectious virus contained in the blood of the subject is destroyed or inactivated. The "subject" may be a human or an animal subject, and is preferably a human subject.

Suitable photosensitizers include but are not limited to phthalocyanines, porphyrins, purpurins, psoralens, bergaptens, angelicins, chlorins and flavins. Particularly preferred photosensitizers are those compounds which absorb in the red region of the visible spectrum such as phthalocyanines. Suitable phthalocyanines include but are not limited to phthalocyanines containing a central atom of aluminum, germanium, gallium, tin or silicon such as silicon phthalocyanine (i.e. hydroxysiloxydimethylpropyl-N-dimethyl silicon phthalocyanine, "Pc4")), as well as sulfonated or nitrated forms of such pthalocyanines, such as sulfonated aluminum phthalocyanine (i.e. aluminum tetra-sulfophthalocyanine ("AlPcS$_4$") or aluminum disulfophthalocyanine ("AlPcS$_{2a}$"). Such phthalocyanines and others are described in Spikes, J. *Photochemistry and Photobiology* 43:691–699 (1986); Ben-Hur, E. and Rosenthal, I. *Int. J. Radiat. Biol.* 47:145–147 (1985); Moser, F. H. and Thomas, A. C. The *Phthalocyanines,* Boca Raton, CRC Press, 1984; Kreimer-Birnbaum, M. *Sem. Hematol.* 26:157–193 (1989); and U.S. Pat. Nos. 5,120,649, 5,232,844 and 5,484,778, which are hereby incorporated by reference in their entirety. In the most preferred embodiment, the phthalocyanine is Pc4.

The photosensitizer may be formulated in the liposome carrier by mixing the desired amount of the photosensitizer with the liposome carrier using procedures well known in the prior art. The liposome carrier may comprise at least one natural phospholipid (e.g. soy phosphatidyl choline), at least one synthetic phospholipid, or combinations thereof. Suitable synthetic liposome carriers include but are not limited to one or more of the following: 1-palmitoyl-2-oleoyl-sn-glycero-phosphocholine (POPC), 1,2-dioleoyl-sn-glycero-3-[phospho-L-serine] (DOPS), 1,2-dioleolyl-sn-glycero-3-phosphate (PA), 1,2-dipalmitoyl-sn-glycero-3-phosphocholine (DPPC), 1,2-distearyl-sn-glycero-3-[phospho-rac-(1-glycerol)] sodium salt (DSPG), and 1,2-distearyl-sn-glycero-3-phosphocholine (DSPC). Preferably, the liposome carrier comprises POPC and DOPS at a ratio of 10:1–0.5:1. Most preferably, POPC and DOPS are used at a ratio of about 4:1, since the inventor has found that this ratio results in the least amount of damage to red blood cells. These and other liposome formulations are discussed in application Ser. No. 08/841,042, filed Apr. 29, 1997, entitled "Methods for Viral Inactivation and Compositions for Use in Same", which is hereby incorporated by reference.

The amount of the photosensitizer administered in the photosensitizer/liposome formulation will depend upon the photosensitizer chosen. However, when the photosensitizer is Pc4, the amount administered is preferably 0.3–3.0 mg/kg body weight, and most preferably is about 1 mg/kg body weight of the subject. The photosensitizer/liposome formulation may be administered by methods known to those skilled in the art, and preferably by transfusion or injection. For such modes of administration, the photosensitizer/liposome formulation may be combined with a pharmaceutically acceptable carrier which is "acceptable" in the sense of being compatible with the other ingredients of the formulation and not deleterious to the recipient thereof. For example, the photosensitizer/liposome formulation may be combined with a sterile aqueous solution which is preferably isotonic with the blood of the recipient. Such formulations may be prepared by combining the photosensitizer/liposome formulation with water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

The light is applied about 10 minutes to about 3 hours, and preferably about 15–60 minutes, after administration of the photosensitizer. The light should be applied at a sufficient wavelength, dose and duration to maximize the inactivation of infectious virus, and at the same time, to minimize the damage to the red blood cells. The inventors have found that if the wavelength of light applied is 20–40 nm greater than the maximum absorption of the photosensitizer, this should be sufficient to maximize the inactivation of infectious virus while minimizing the damage to the red blood cells. For example, when the photosensitizer is Pc4, it is preferred that the light be applied at a specific wavelength somewhere in the range of 695–705 nm, and most preferably at a specific wavelength of about 700 nm.

The specific dose and duration of light again will depend upon the photosensitizer chosen. When the Pc4 is the photosensitizer, the dose of light applied is preferably about 5–25 mW/cm$^2$, and most preferably about 18–22 mW/cm$^2$, while the duration of light application is about 5–60 minutes, and most preferably about 20–30 minutes. Suitable sources of light include commercially available lasers, lamps, light emitting diodes and the like. Preferably, a LED arrays (Efos Canada, Inc., Mississauga, Ontario, Canada) is employed. To achieve the desired wavelength of light, the lamp may be equipped with commercially available filters.

It also is within the confines of the present invention that one or more quenchers can be administered before, during or after the administration of the photosensitizer/liposome formulation, but before application of light. Suitable quenchers include but are not limited to glutathione, trolox, flavonoids, vitamin C, vitamin E, cysteine and ergothioneine and other non-toxic quenchers, and preferably vitamin E. The amount of the quencher administered will depend upon the specific quencher(s) chosen and can be determined by one skilled in the art. However, when the quencher is vitamin E, the preferred dose ranges from about 10 mg/kg body weight to about 1 g/kg body weight, and most preferably about 100 mg/kg body weight.

In addition, it is within the confines of the present invention that one or more quenchers can be formulated in a liposome carrier to enhance the association of the quencher to the red blood cells, thus affording a more selective protection to the red blood cells. Suitable liposome carriers include those carriers that enhance delivery of the quencher to the red blood cells, such as liposomes containing cholesterol, liposomes made from natural phospholipids (e.g. soy phosphatidyl choline (PC)), and POPC. Preferably, the quencher is vitamin E, and the liposome carrier is POPC. When using vitamin E and POPC, the preferred vitamin E:POPC ratio is 1:5–1:3, and most preferably is about 1:3.7.

The present invention is described in the following Examples which are set forth to aid in an understanding of the invention, and should not be construed to limit in any way the invention as defined in the claims which follow thereafter.

EXAMPLE 1

Preparation of Pc4 in Liposomes

HOSiPcOSi(CH$_3$)$_2$(CH$_2$)$_3$N(CH$_3$)$_2$ (Pc4) (1 mg) was dissolved in 0.5 ml of N-methylpyrolidone (NMP) prewarmed to 50° C. and sonicated 1–2 minutes. 1-palmitoyl-2-oleoyl-sn-glycero-phosphocholine (POPC) (90 mg) was dissolved in tert-butyl alcohol (0.5 ml), and prewarmed to 50° C. Similarly, 1, 2-dioleoyl-sn-glycero-3-phospho-L-serine (DOPS) (10 mg) was dissolved in tert-butyl alcohol (0.5 ml), and prewarmed to 50° C. The solutions were then sonicated at 50° C. until complete dissolution occurred. The phospholipid solutions were combined and kept at 50° C. The Pc4 solution was combined with the phospholipid solution at 50° C. to achieve a ratio of Pc4:phospholipid=1:100 (w/w). This was mixed with excess (16×) of aqueous solution containing 9.45% D-lactose and 0.027% NaCl. Prior to mixing, the organic solution should be at 50° C. and the aqueous solution at 4° C. The former was added dropwise into the latter with vigorous stirring. Stirring was continued for 15 minutes at 4° C. The resulting liposomal suspension was concentrated (10×) with 100 kDa Amicon concentrator and centrifuged at 3000 rpm at room temperature. The remaining organic solvents were removed by dialysis against lactose/NaCl solution at 4° C. using a dialysis membrane with a MW cutoff of 6000–8000. The dialysis solution was changed 3× every few hours. The final liposomal solution of Pc4 was lyophilized and stored at 4° C. Prior to use, the liposomes were dissolved in phosphate buffered saline (PBS) using a vortex for mixing followed by 1–2 minutes of sonication.

EXAMPLE 2

VSV In Vitro Study

The inactivation kinetics of vesicular stomatitis virus (VSV) in whole blood and plasma with liposomal Pc4 and 700 nm light was studied. These kinetics are identical to that of HIV (Margolis-Nunno, H., et al. *Transfusion* 36:743–750 (1996)). Whole blood and plasma samples were spiked with 6.3 and 6.1 log$_{10}$ of VSV, respectively. The whole blood sample was then treated with the Pc4 liposome composition prepared in Example 1 to a Pc4 concentration of 2 µM. The plasma sample was treated with the Pc4 liposome to a Pc4 concentration of 2 µM, and also with 4 mM GSH and 5 mM trolox. Using an LED array (Efos Canada, Inc., Mississauga, Ontario, Canada) emitting at 700 nm, light was applied to the whole blood and plasma samples at various light fluences (J/cm$^2$) at a fluence rate of 20 mW/cm$^2$. The results are presented in FIG. 1. The majority of the VSV contained in the plasma was killed at light fluences greater than 2 J/cm$^2$, while similar virus kill in the whole blood was obtained with a fluence greater than 6 J/cm².

EXAMPLE 3

Evaluation of RBC Damage

Figure 2:
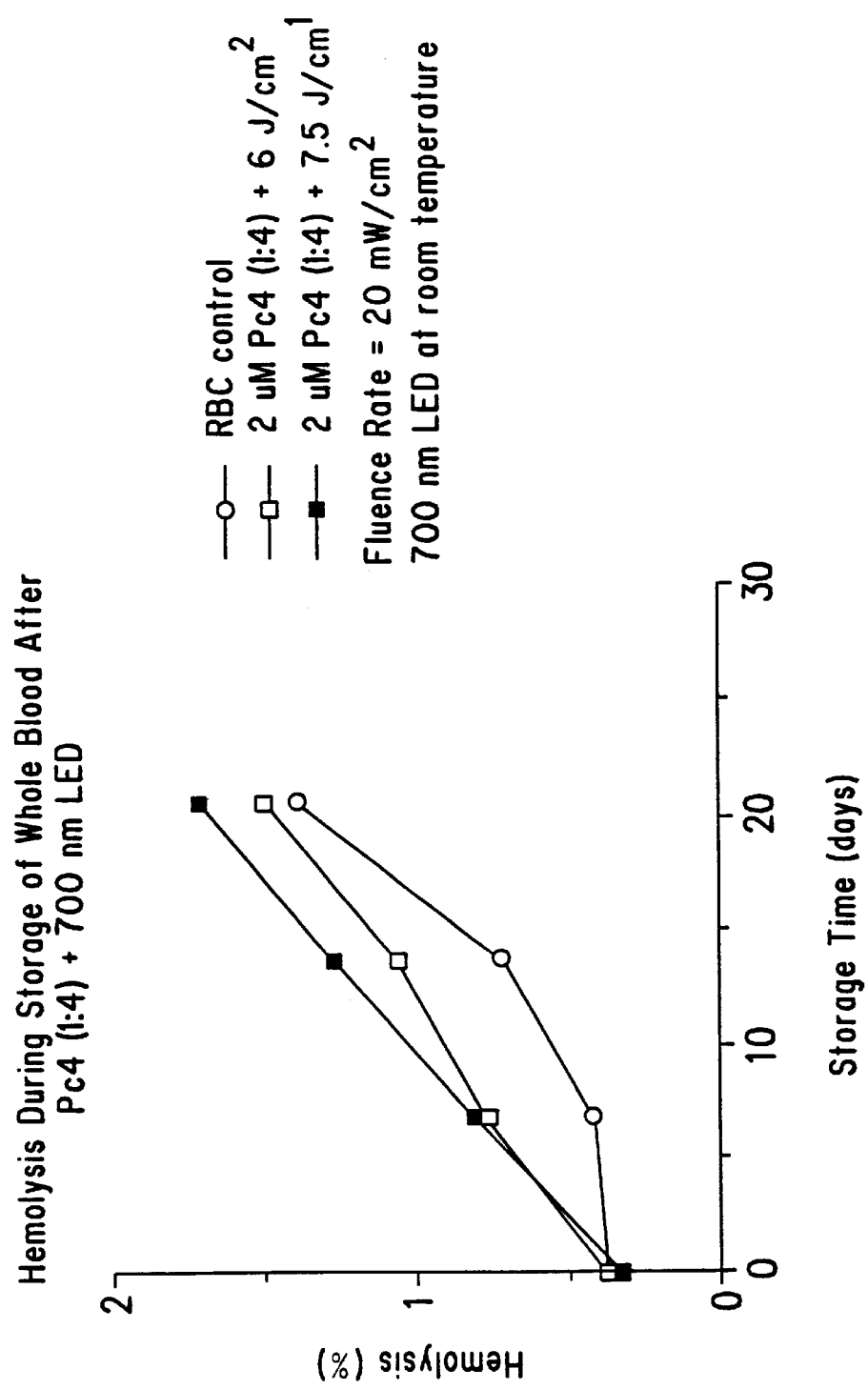
FIG. 2 depicts the extent of hemolysis of red blood cells in storage following treatment with liposomal 2 µM Pc4 and 700 nm light at 6 J/cm² (□) or 7.5 J/cm² (■), at a fluence rate of 20 mW/cm² at room temperature. Untreated RBC was the control (○).

Whole blood was treated with the Pc4 liposome composition prepared in Example 1 to a Pc4 concentration of 2 μM. 700 nm light was then applied at doses that inactivate ≧6 $\log_{10}$ VSV (6 and 7.5 J cm²), and stored at 4° C. The extent of RBC hemolysis during storage was determined by comparing the hemoglobin in the supernatant to the total hemoglobin. The total hemoglobin was determined by using the Drabkin reagent (Sigma Procedure #525, Sigma Chemical Co., St. Louis, Mo.). The absorption at 540 nm was used to calculate the amount of hemoglobin released in the supernatant. The results are presented in FIG. 2 and show no significant hemolysis of the treated RBC over that of control, untreated RBC.

EXAMPLE 4

HIV In Vitro Study

Whole blood spiked with >5 $\log_{10}$ HIV was treated with the Pc4 liposome composition prepared in Example 1 to a Pc4 concentration of 2 μM. Using an LED array emitting at 700 nm, light was applied to the whole blood at various light fluences (J/cm²) at a fluence rate of 20 mW/cm². HIV titer was assayed as described (Margolis-Nunno, H., et al. *Transfusion* 36:743–750 (1996)). The results are presented in FIG. 3, and show a significant reduction of HIV titers at a light fluence of 8 J/cm².

EXAMPLE 5

The Use of Quenchers In Vitro

RBCC were treated with 2 μM Pc4 in POPC:DOPC=4:1 liposomes in the presence of 1 mM tocopherol succinate in the formulations presented in Table 1 below, and exposed to 10 J/cm² of red light (670 nm) emitted by LED array. The RBCC were then stored for 21 days at 4° C. The percentage of hemolysis for each formulation is presented in Table 1 below.

TABLE 1

| Formulation of α-tocopherol succinate (1 nM) | Hemolysis After 21 Day Storage (%) |
|---|---|
| Ethanol | 10.5 |
| POPC:DOPS = 4:1 | 18.3 |
| POPC:DOPS:chol = 9:1:10 | 6.1 |
| POPC | 1.2 |
| Untreated RBCC | 1.1 |

EXAMPLE 6

In Vivo Study

Mice were administered liposomal Pc4 at 1 mg/kg body weight, their backs were shaved and then exposed to 700 nm light at 20 mW/cm², 15 minutes after Pc4 administration. The mice tolerated this treatment for up to 30 minutes illumination with no adverse effects. This treatment is expected to cause sufficient exposure of the circulating blood to reduce viremia in plasma by ≧6 $\log_{10}$.

All publications and patents mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed:

1. A method for treating a viral infection in a subject in need of such treatment comprising administering to the blood of the subject (i) a photosensitizer formulated in a first liposome carrier and (ii) at least one quencher, and exposing the subject to light at a sufficient wavelength, dose and duration to treat the viral infection in the subject;

said first liposome carrier comprising 1-palmitoyl-2-oleoyl-sn-glycero-phosphocholine (POPC) and 1,2-dioleoyl-sn-glycero-3-(phospho-L-serine) (DOPS) at a ratio of 10:1–0.5:1.

2. The method of claim 1, wherein the viral infection is caused by a virus selected from the group consisting of human immunodeficiency virus, Cytomegalovirus, Ebstein-Barr virus, Hepatitis B virus, Hepatitis C virus, and Herpes Simplex viruses.

3. The method of claim 2, wherein the virus is human immunodeficiency virus.

4. The method of claim 1, wherein the photosensitizer is selected from the group consisting of a phthalocyanine, a porphyrin, a purpurin, a psoralen, a bergapten, an angelicin, a chlorin, and a flavin.

5. The method of claim 4, wherein the photosensitizer is a phthalocyanine.

6. The method of claim 5, wherein the phthalocyanine is an aluminum, germanium, gallium, tin or silicon phthalocyanine; a sulfonated-aluminum, germanium, gallium, tin or silicon phthalocyanine; or a nitrated-aluminum, germanium, gallium, tin or silicon phthalocyanine.

7. The method of claim 6, wherein the phthalocyanine is a sulfonated aluminum phthalocyanine.

8. The method of claim 7, wherein the sulfonated aluminum phthalocyanine is aluminum tetrasulfophthalocyanine or aluminum disulfophthalocyanine.

9. The method of claim 6, wherein the phthalocyanine is a silicon phthalocyanine.

10. The method of claim 9, wherein the silicon phthalocyanine is hydroxysiloxydimethylpropyl-N-dimethyl silicon phthalocyanine (Pc4).

11. The method of claim 1, wherein the ratio of POPC to DOPS is about 4:1.

12. The method of claim 1, wherein the phthalocyanine formulated in the first liposome carrier is administered by transfusion or injection.

13. The method of claim 1, wherein the quencher is selected from the group consisting of flavonoids, vitamin C, vitamin E, glutathione, trolox, cysteine, ergothioneine, and other non-toxic quenchers.

14. The method of claim 13, wherein the quencher is formulated in a second liposome carrier.

15. The method of claim 14, wherein the second liposome carrier comprises at least one natural phospholipid, at least one synthetic phospholipid, or combinations thereof.

16. The method of claim 15, wherein the second liposome carrier comprises cholesterol.

17. The method of claim 15, wherein the second liposome carrier comprises soy phosphatidyl choline (PC).

18. The method of claim 15, wherein the second liposome carrier comprises 1-palmitoyl-2-oleoyl-sn-glycero-phosphocholine (POPC).

19. The method of claim 18, wherein the quencher is vitamin E.

20. The method of claim 19, wherein the ratio of vitamin E to POPC is 1:5–1:3.

21. The method of claim 19, wherein the ratio of vitamin E to POPC is about 1:3.7.

22. The method of claim 1, wherein the quencher is administered before, during or after administration of the photosensitizer formulated in the first liposome carrier.

23. The method of claim 1, wherein the light is applied at a wavelength 20–40 nm greater than the maximum absorption of the photosensitizer.

24. The method of claim 1, wherein the light is applied about 10 minutes to about 3 hours after administering the photosensitizer formulated in the first liposome carrier.

25. The method of claim 1, wherein the light is applied about 15–60 minutes after administering the photosensitizer formulated in the first liposome carrier.

26. The method of claim 10, wherein the amount of Pc4 administered is about 0.3–3.0 mg/kg body weight of the subject.

27. The method of claim 10, wherein the amount of Pc4 administered is about 1 mg/kg body weight.

28. The method of claim 10, wherein the wavelength of light applied is about 695–705 nm.

29. The method of claim 10, wherein the wavelength of light applied is about 700 nm.

30. The method of claim 10, wherein the dose of light applied is about 5–25 mW/cm$^2$.

31. The method of claim 10, wherein the dose of red light is about 18–22 mW/cm$^2$.

32. The method of claim 10, wherein the light is applied for about 5–60 minutes.

33. The method of claim 10, wherein the light is applied for about 20–30 minutes.

* * * * *